(12) United States Patent
Bonnema et al.

(10) Patent No.: US 8,928,888 B2
(45) Date of Patent: *Jan. 6, 2015

(54) SWEPT SOURCE OPTICAL COHERENCE TOMOGRAPHY (OCT) METHOD AND SYSTEM

(71) Applicant: D4D Technologies, LLC, Richardson, TX (US)

(72) Inventors: Garret T. Bonnema, Richardson, TX (US); Henley S. Quadling, Dallas, TX (US); Mark S. Quadling, Plano, TX (US)

(73) Assignee: D4D Technologies, LLC, Richardson, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/729,643

(22) Filed: Dec. 28, 2012

(65) Prior Publication Data

US 2013/0182260 A1 Jul. 18, 2013

Related U.S. Application Data

(63) Continuation of application No. 12/762,511, filed on Apr. 19, 2010, now Pat. No. 8,345,257.

(60) Provisional application No. 61/170,886, filed on Apr. 20, 2009, provisional application No. 61/172,513, filed on Apr. 24, 2009, provisional application No. 61/173,714, filed on Apr. 29, 2009.

(51) Int. Cl.
*G01B 9/02* (2006.01)

(52) U.S. Cl.
USPC .......................................................... 356/477

(58) Field of Classification Search
USPC ......................................... 356/477, 479, 497
See application file for complete search history.

(56) References Cited

U.S. PATENT DOCUMENTS

| 2003/0218756 | A1* | 11/2003 | Chen et al. | 356/497 |
| 2007/0015969 | A1* | 1/2007 | Feldman et al. | 600/160 |
| 2007/0146726 | A1* | 6/2007 | Quadling et al. | 356/602 |
| 2010/0097616 | A1* | 4/2010 | Nebosis et al. | 356/477 |

* cited by examiner

*Primary Examiner* — Gregory J Toatley
*Assistant Examiner* — Dominic J Bologna
(74) *Attorney, Agent, or Firm* — David H. Judson

(57) ABSTRACT

A method and apparatus are provided for a swept source optical coherence tomography (OCT) system utilizing a fast scanning mechanism in the sample arm and a slowly swept light source. The position data is collected rapidly while the wavelength of the source is swept slowly. The system reduces the sweep speed requirements of the light source enabling higher power, greater imaging range, and linear sweeps of the source frequency. The OCT components (or most of them) may be implemented within a hand held imaging probe. In operation, a triangulation scan may be used to orient the imaging probe with respect to a fixed coordinate system; preferably, OCT data captured by the device is then transformed to that same orientation with respect to the fixed coordinate system to improve the scanning results.

5 Claims, 3 Drawing Sheets

SWEPT SOURCE OPTICAL COHERENCE TOMOGRAPHY (OCT) METHOD AND SYSTEM

This application is based on Ser. No. 12/762,511, filed Apr. 19, 2010, now U.S. Pat. No. 8,345,257, which application was based on and claimed priority from Ser. No. 61/170,886, filed Apr. 20, 2009, Ser. No. 61/172,513, filed Apr. 24, 2009, and Ser. No. 61/173,714, filed Apr. 29, 2009.

BACKGROUND

Optical coherence tomography (OCT) is a depth-resolved imaging modality. Reflections of light returning from within the tissue are used to create tomograms of the tissue microstructure.

A known OCT system is described in U.S. Pat. No. 7,355,721. The OCT imaging system described there includes a light source, an optical coupler or beam splitter, a reference arm, a projector, and a sensor. The OCT imaging system also may be coupled to a processor.

An alternative OCT technique uses a swept source. In one known implementation, the wavelength or frequency of a laser is swept over a range supported by the laser's gain medium. This form of OCT is called swept source OCT or optical coherence domain reflectometry (OCDR).

A standard swept source OCT system is illustrated in FIG. 1. The source 100 emits light within the visible and infrared regions of the electromagnetic spectrum. At any instant of time, a laser with a narrowband of wavelengths is emitted from the light source. The source uses a spectral filter within the cavity to control the laser wavelength. The range of emitted wavelengths is dependent on a gain medium of the source. An exemplary swept source emits a laser with an instantaneous line width of 0.1 nm that is swept from 1250 to 1350 nm.

A circulator 102 directs light from the swept source to a 2×2 coupler 104. The 2×2 coupler splits and directs a portion of the light to the reference and sample arms (106, 108) of a Michelson interferometer. The reference arm 106 provides a fixed optical path length. The sample arm 108 has approximately the same optical path length as the reference arm 106. The sample arm includes optical and scanning elements necessary to focus and position the beam into tissue. Light reflecting from the two arms are combined at the 2×2 coupler. The two beams containing the interfering signals are sent to a dual balanced detector 110. The data is then acquired and processed using a computer (not shown). This processing may include re-sampling of the waveform and Fourier transformation.

In the prior art, the sweep rate of the light source governs the image acquisition rate of the OCT system. Each sweep of the source corresponds to one column, that is, an axial scan, through the tissue. A slower lateral scan within the sample arm is used to collect multiple axial scans for a 2D image. This process is illustrated in FIG. 2. At one position of a scan mirror 200, a data acquisition system (not shown) acquires the interference signal as a function of the wavelength (or frequency) emitted by the swept source. The process occurs for each subsequent position of the scan mirror until enough axial scans are recorded for a 2D image.

As shown in FIG. 3, the swept source OCT system produces a two dimensional matrix 300 with wavelength represented in the $1^{st}$ dimension and lateral position in the $2^{nd}$ dimension. In this system of the prior art, this matrix 300 is populated by acquiring each column 302 sequentially. A computer is often used to resample and Fourier transform each column of the data matrix.

In the prior art OCT system, a greater sweep rate is required from the swept laser to image with greater speed. Sweeping a laser at a fast rate, however, often comes with negative consequences. When the sweep rate increases, the light travels less through the gain medium resulting in a decrease in the optical power emitted by the source. The instantaneous line width of the source can be increased to provide more optical power, but this reduces the useful imaging range of the OCT instrument.

The subject matter of this disclosure addresses these and other deficiencies of the prior art.

BRIEF SUMMARY

A method and apparatus are provided for a swept source optical coherence tomography (OCT) system utilizing a fast scanning mechanism in the sample arm and a slowly swept light source. The position data is collected rapidly while the wavelength of the source is swept slowly. The system reduces the sweep speed requirements of the light source, enabling higher power, greater imaging range, and linear sweeps of the source frequency.

According to another feature of the disclosed subject matter, the sample, reference, and detection arms of an OCT interferometer are incorporated into an imaging probe, preferably using freespace optical elements.

According to still another feature, preferably a triangulation scan is used to orient the imaging probe device with respect to a fixed coordinate system, and OCT data is transformed to that same orientation with respect to the fixed coordinate system. This approach enables a dental imaging system to provide 3D digitizing using OCT with triangulation-based registration of multiple scans, preferably from a hand held device.

Other features and advantages of the disclosed subject matter will be apparent to one with skill in the art upon examination of the following figures and detailed description. It is intended that all such additional features and advantages be included within this description, be within the scope of the disclosure, and be protected by the claims.

BRIEF DESCRIPTION OF THE DRAWINGS

The subject matter herein can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DISCLOSURE OF AN EMBODIMENT

In this disclosure, in contrast, multiple lateral scans over the same area preferably are performed during a wavelength sweep of the light source. Preferably, the lateral scan is performed with resonant scanning mirrors or polygonal scanning mirrors. In this arrangement, the OCT system becomes limited only by the lateral scan speed of the sample arm rather than the sweep speed of the light source. Preferably, multiple lateral scans are performed over the same region. During each lateral scan, the wavelength of the source remains nearly constant. The wavelength of the source changes for each subsequent lateral scan. For each position along the lateral scan, the interference signal is recorded versus the wavelength or frequency of the swept source.

In the prior art, a laser sweep rate typically is a product of a frame rate (images/second) and a number of axial scans per image. A sweep rate of this light source herein preferably is the laser scan rate on the specimen divided by a number of wavelength samples. The approach described herein permits the same imaging frame rates with a laser sweep rate several orders of magnitude slower as compared to the prior art. For example, assume that 1000 axial scans are needed for an image and that each axial scan consists of 1000 samples at different wavelengths. To acquire the image at 60 frames per second, the prior art light source would need to sweep through the gain medium's wavelength range at 60 kHz (1000×60). In the approach herein, however, the light source sweeps through its wavelength range at 60 Hz.

Figure 1:
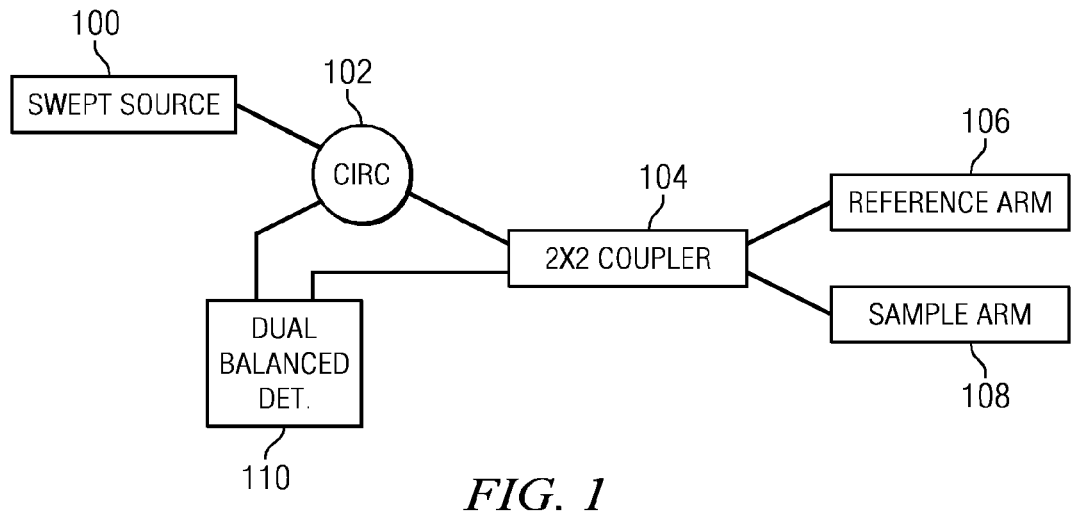
FIG. 1 illustrates a known swept source optical coherence tomography ("OCT") imaging system.
Figure 2:
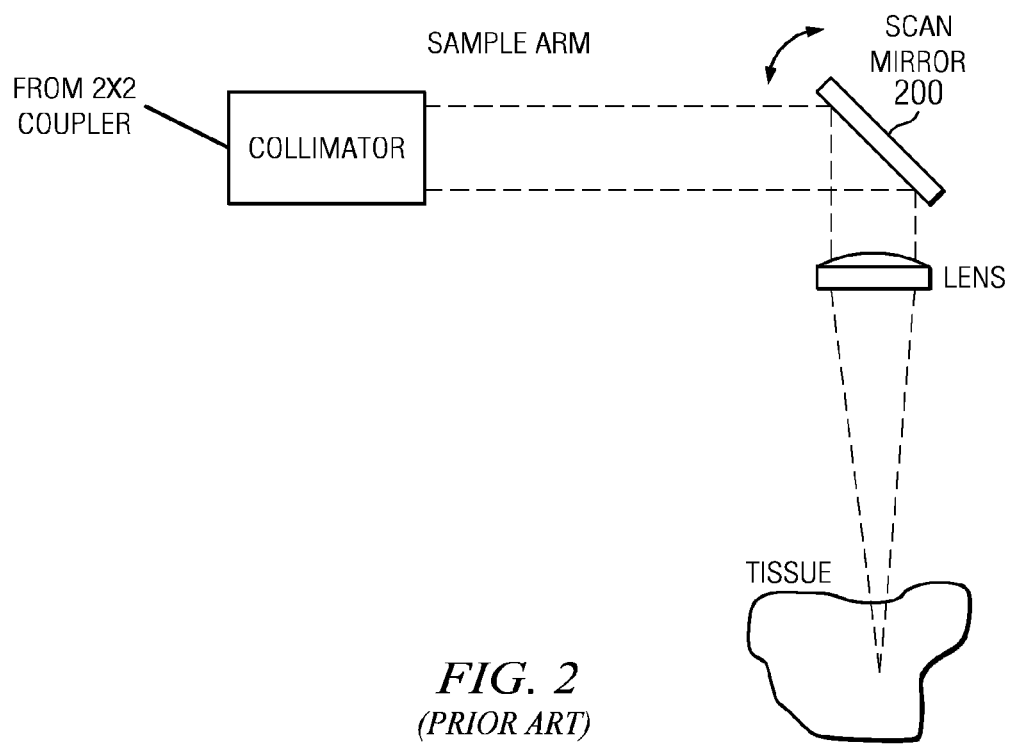
FIG. 2 illustrates the sample arm optics and imaging technique used in the OCT imaging system of FIG. 1.
Figure 3:
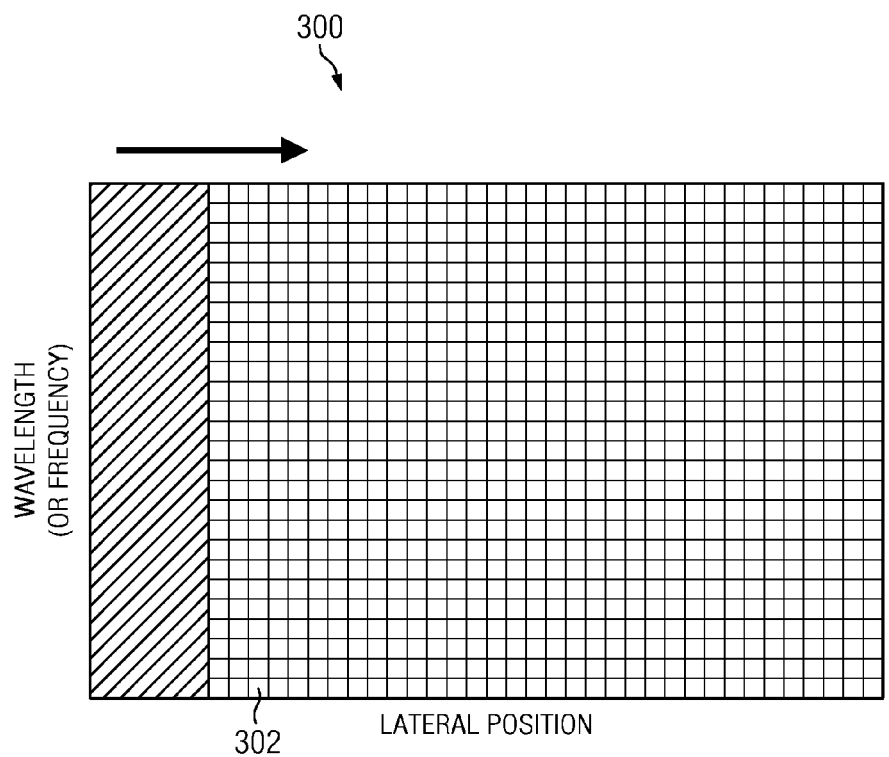
FIG. 3 illustrates a two (2) dimensional matrix generated using the known swept source OCT imaging system.
Figure 4:
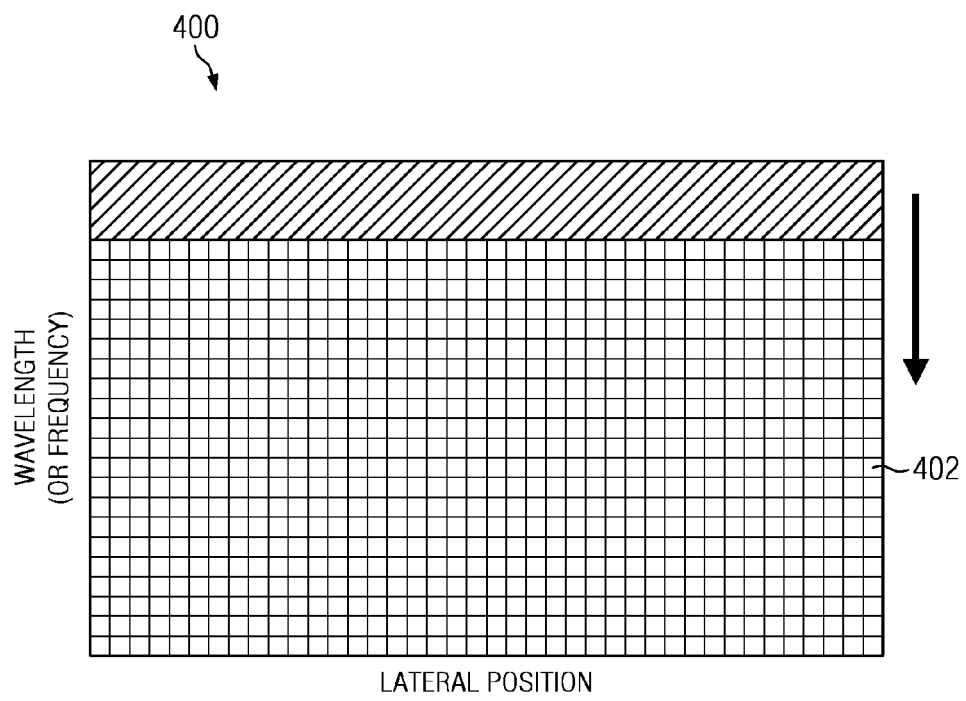
FIG. 4 illustrates a two (2) dimensional matrix generated according to the teachings of this disclosure.

FIG. 4 demonstrates the difference between this disclosure and the prior art with the construction of the data matrix. According to the technique described in this disclosure, a row 402 of the matrix 400 is populated during one lateral scan in the sample arm. Each subsequent lateral scan occurs at a different wavelength (or frequency) until the entire sweep of the source is complete. The data is the same as the prior art and the same processing occurs, however, the data acquisition method is distinctly different and provides significant advantages.

In particular, this technique provides several key advantages over the prior art. As noted above, for a given frame rate and image size, this present approach enables slower wavelength sweep speeds as compared to the prior art. The slower sweep speeds as contemplated herein allow the light to travel many times through the gain media. This maximizes the amount of light amplification, which results in greater optical intensities emitted from the source. Further, as the light has time to make many passes through the gain media, the instantaneous line width of the spectral filter within the source cavity can be reduced. This reduced instantaneous line width results in greater imaging range of the swept source.

To provide high sweep rates, swept source technologies generally have non-linear scans through optical frequency. The "slower" sweep rates of the disclosed technique permit linear sweeps with wavelength or optical frequency. Linear sweeps can simplify signal re-sampling techniques associated with prior art swept source OCT systems.

An illustrative commercial swept source that may be adapted to practice the technique described above is the HSL-2100 from Santec Corporation. Other alternatives include, without limitation, the SS225 from Micron Optics, and the SL1325-P16 from Thorlabs. These are merely representative.

The subject disclosure may be implemented using base OCT technologies, such as the optical elements and related processing devices and sub-systems such as described in U.S. Pat. No. 7,355,721, the disclosure of which is incorporated herein by reference.

In addition, the disclosed subject matter may be implemented is conjunction with a computer workstation that comprises hardware, suitable storage and memory for storing an operating system, one or more software applications and data, conventional input and output devices (a display, a keyboard, a mouse, etc.), other devices to provide network connectivity, and the like. Optical elements such as described in U.S. Pat. No. 7,184,150 may be implemented as needed.

Figure 5:
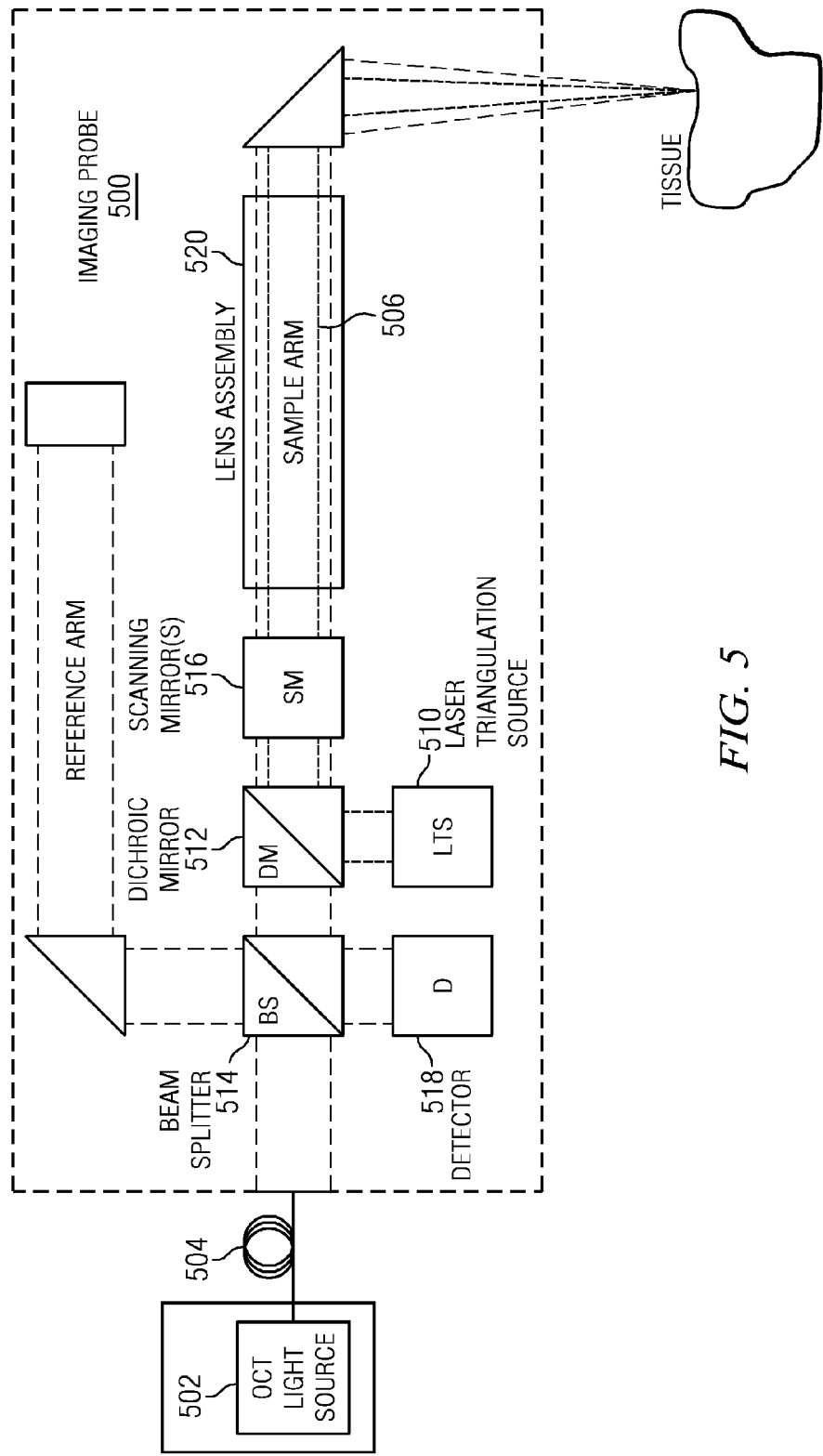
FIG. 5 illustrates an imaging probe that comprises a set of OCT optical elements that implement a swept source scanning technique.

FIG. 5 illustrates another aspect of the disclosed invention. In this embodiment, a hand held imaging probe 500 is connectable to an OCT light source 502 through an optical fiber 504, and the imaging probe is used to capture the OCT data. In this approach, and as can be seen in FIG. 5, preferably the sample, reference, and detection arms of the OCT interferometer are incorporated into the imaging probe using freespace optics. Representative freespace optics are available commercially from various suppliers including, without limitation, Thorlabs, Newport, and Edmund Optics.

Although not a limitation of this disclosure, preferably a triangulation scan is used to orient the imaging probe device of FIG. 5 with respect to a fixed coordinate system, and the OCT data collected by that device is transformed to that same orientation with respect to the fixed coordinate system. Thus, using the device shown in FIG. 5, a dental imaging system may provide 3D digitizing using OCT with triangulation-based registration of multiple scans.

To this end, the imaging probe comprises sample arm 506, reference arm 508, laser source 510, dichroic mirror 512, beam splitter 514, scanning mirrors 516 and detector 518. Inside the imaging probe, the light is collimated and then split into the reference and sample arms of the OCT system. This is performed by either a freespace beamsplitter 514 or a fiber optic 2×2 coupler. Light in the reference arm is directed to a mirror using a combination of prisms and lenses (not shown). The mirror is positioned such that the optical path length of the reference arm is approximately equal to the sample arm path length. The beam of the sample arm passes through the dichroic mirror 512. As noted above, preferably this device combines the OCT light and laser triangulation (LT) light into one beam. The combined OCT/LT beam is reflected by one or more scanning mirrors 516. These mirrors enable the beam to be scanned across the surface of the tissue. The scanned beam is transmitted to the distal end of the probe using a lens assembly 520. The lens assembly is designed to accommodate the scan angles and different wavelength bands of the OCT and LT subsystems. The lenses are also used to focus the beam near the tissue surface. A prism deflects the beam towards the tissue.

In general, the scanning technique combines both methods described above into a single device (such as shown in FIG. 5) and describes the means to combine the various types of 3D data into a single unified data set.

Using the combined device, the oral cavity of a patient may be scanned as follows:

In the first step, the device is configured to scan in triangulation mode. Using this mode, the patient's full mouth may be fully scanned within minutes using the high speed triangulation method. When this operation has been completed, a 3D mesh S of all the directly-visible surfaces in the oral cavity is computed and displayed on a computer screen. Following this, the device is configured to be scanned in the OCT mode. Using this mode, the device is positioned to obtain additional volume data in the desired location of an area that was previously scanned. When triggered, the scanner then performs a single detailed OCT scan of the region, which we shall refer to as C. Preferably, C is a volume of densities on a three dimensional grid where each grid location has a position coordinate with respect to the origin of the camera. i.e., if C is a grid of nx by ny by nz values, then each position C [x,y,z] (where x=[1, . . . , nx], y=[1, . . . , ny], z=[1, . . . , nz]) corresponds to a 4-tuple (a,b,c,d) where (a,b,c) is a position of the grid point in space relative to the origin of the device, and d is the density at that location as imaged.

The scanner also performs a single triangulation-based scan in that same position, which we shall refer to as T. Preferably, T is a two dimensional grid of position coordinates. i.e., if T is a grid of nx by ny values, then each position T[x,y] ((where x=[1, . . . , nx], y=[1, . . . , ny]) corresponds to a triple (a,b,c) which is the position of the grid point in space relative to the origin of the device.

Note that the OCT scan obtains a three dimensional grid of densities at locations in space, whereas the triangulation scan only obtains a two dimensional grid of locations in space. This is due to the fact that the triangulation method is only able to see surfaces, whereas the OCT method is able to see below the surface.

It is then possible to compute a 4×4 matrix M which when applied to T, transforms the points T to correspond to the same equivalent points in the mesh S as computed during the previous triangulation only scanning process. This is done using the same process that is used to register triangulation scans together, in other words by using a method such as ICP (iterative closest pair matching).

We further assume that the device has moved only minimally during this process and so we may then use the matrix M obtained above to transform the volume grid C into the same coordinate space as the mesh C.

When this process is repeated a number of times, we obtain a collection of volume grids that are positioned spatially in their correct orientations relative to each other even if the OCT scans are non-overlapping.

These multiple grids may then be combined into a single spatial grid (for example, where there is no data from any constituent scan C, the density may be indicated as zero). This approach allows us to effectively use the OCT technique over a large volume using a much smaller OCT scanning volume by merging multiple OCT scans together.

Thus, and although not meant to be limiting, preferably a laser triangulation contouring system is included in the imaging probe design. This technique addresses the problem of locating the OCT data when imaging in a confined area. Preferably, laser triangulation provides 3D registration of the OCT data.

The above-described laser triangulation and OCT data capture technique is not limited for use with the hand held imaging probe of FIG. 5, as the techniques may be implemented in other devices or systems.

Using the above-described technique, the user may scan areas of interest in the oral cavity using the superior scanning ability of the OCT technique, and have all the separate scans be registered correctly with respect to each other. Such a database can then be used very beneficially in dentistry. For example, such a database could be used to catalog all the different materials present in the mouth of a patient, by tooth. Such materials could include different restoration materials (such as ceramics, composites, metals, etc). The database could be used to locate caries both at the surface, or interproximally, or even underneath existing non-metal restorations. The database could be used to feature tartar deposits, plaque deposits or perio pocket depths. By comparing databases over time (for example comparing the data base to that of the same patient six months prior), it would also be possible to track changes such as gum loss. By combining these two technologies within a single device (which enables their data to be registered to each other), it is possible to include diagnostic information within the 3D data set. The diagnostic information is obtained from the volumetric nature of the OCT-derived data as well as the ability of OCT to identify interfaces between materials as well as relative and absolute densities of materials on the surface and volumetrically. This enables the technology to provide a 3D diagnostic map, including but not limited to, caries detection (decay), cancer detection, inflammation, gum disease, periodontal disease and other disease and injuries, as well as keep track of changes in the above over time, thereby assisting in the diagnosis and tracking the oral health of the patient.

The database could also be used to produce restorations, which have traditional been designed using triangulation data only. For example, a preparation where the margin is subgingival can now be done with ease, because the margin will now be fully visible even if hidden from direct sight by biological tissue as long as that tissue is no more than about 5 mm thick. An example of such an application is the scanning of a subgingival implant abutment. Due to the surgical nature of the implant procedure, it usually is not possible to digitize the implant abutment fully when it has been inserted into the cavity. By utilizing a technology than can scan surfaces through biological tissues and fluids, it will be possible to design CAD/CAM restorations to fit on implant abutments within a single visit.

While certain aspects or features of the disclosed subject matter have been described in the context of a computer-based method or process, this is not a limitation of the invention. Moreover, such computer-based methods may be implemented in an apparatus or system for performing the described operations, or as an adjunct to other dental restoration equipment, devices or systems. This apparatus may be specially constructed for the required purposes, or it may comprise a computer selectively activated or reconfigured by a computer program stored in the computer (in which case it becomes a particular machine). Such a computer program may be stored in a computer readable storage medium, such as any type of disk including optical disks, CD-ROMs, and magnetic-optical disks, read-only memories (ROMs), random access memories (RAMs), magnetic or optical cards, or any type of media suitable for storing electronic instructions, and each coupled to a computer system bus. The described functionality may also be implemented in firmware, in an ASIC, or in any other known or developed processor-controlled device.

While the above describes a particular order of control operations performed by certain embodiments, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic. Further, while given components of the system have been described separately, one of ordinary skill will appreciate that some of the functions may be combined or shared in given systems, machines, devices, processes, instructions, program sequences, code portions, and the like.

Having now described our invention, what we claim is as follows:

1. A method of scanning an object using a light source, comprising:
    (a) triangulation scanning the object to produce a mesh in a fixed coordinate system;
    (b) at each of one or more scan locations overlapping with the mesh, performing a scan in triangulation mode, and a scan in optical coherence tomography (OCT) mode;

(c) computing, using software executing in a hardware element, a transformation matrix that registers the scan in triangulation mode with the mesh;

(d) applying the transformation matrix to data collected from the scan in OCT mode to generate transformed OCT data; and (e) merging the transformed OCT data into a mesh that is in the fixed coordinate system.

2. The method as described in claim 1 wherein the scan in OCT mode comprises at least first and second lateral scans over an area to be imaged as a wavelength of the light source is swept.

3. The method as described in claim 2 wherein during a first lateral scan the wavelength of the light source has a first, substantially constant value, wherein during a second lateral scan the wavelength of the light source has a second, substantially constant value, where the first and second values differ.

4. The method as described in claim 1 wherein the light source is a slowly-swept light source.

5. The method as described in claim 1 wherein the object is a dental object.

\* \* \* \* \*